United States Patent [19]

Green et al.

[11] Patent Number: 5,324,502
[45] Date of Patent: Jun. 28, 1994

[54] RADIOPHARMACEUTICALS FOR IMAGING THE HEART

[75] Inventors: Mark A. Green, West Lafayette; Brenda W. Tsang, Lafayette, both of Ind.

[73] Assignee: Purdue Research Foundation, West Lafayette, Ind.

[21] Appl. No.: 861,778

[22] Filed: Apr. 2, 1992

[51] Int. Cl.$^5$ ...................... A61K 49/02; A61K 43/00
[52] U.S. Cl. .................................... 424/1.81; 534/10; 534/14; 424/1.85
[58] Field of Search .................. 424/1.1, 9; 556/1, 32; 534/10

[56] References Cited

U.S. PATENT DOCUMENTS 5,101,041  3/1992  Troutner et al. .................... 548/518

OTHER PUBLICATIONS

Chemical Abstracts: CA77(24)159507G Polarographic studies on Cobalt Chelate Complexes (1972).
Fritz et al., Z. Anorg. Allg. Chem. (1972) vol. 392, No. 3, pp. 271-278.
"Synthesis And Biodistribution Of A Series Of Lipophilic Gallium-67 Tris (Salicylaldimine)".
"A New Myocardial Imaging Agent: Synthesis, Characterization, and Biodistribution of Gallium-6-8-BAT-TECH", The Journal of Nuclear Medicine, vol 31, No. 10, Oct. 1990, by H. F. Kung, et al., pp. 1635-1640.
"Gallium-68, 1,1,1-Tris (5-Methoxysalicylaldiminomethyl) Ethane: A Potential Tracer for Evaluation of Regional Myocardial Blood Flow", The Journal of Nuclear Medicine, vol. 26, No. 2, Feb. 1985, by M. A. Green, et al., pp. 170-180.
"Copper-62-Labeled Pyruvaldehyde Bis(N$^4$-methylthiosemicarbazonato)copper(II): Synthesis and Evaluation as a Positron Emission Tomography Tracer for Cerebral and Myocardial Perfusion", M. A. Green, et al., The Journal of Nuclear Medicine, vol. 31, No. 12, Dec. 1990, pp. 1989-1996.
"The Potential for Generator-Based PET Perfusion Tracers", M. A. Green, The Journal of Nuclear Medicine, vol. 31, No. 10, Oct. 1990, pp. 1641-1645.
"Myocardial Perfusion with Rubidium-82. II. Effects of Metabolic and Pharmacologic Interventions", R. A. Goldstein, et al., The Journal of Nuclear Medicine, vol. 24, No. 10, 1983, pp. 907-915.
"Overview: Diagnosis of Ischemic heart Disease by Noninvasive Techniues", M. H. Crawford, M.D., Circulation, 1991; 84 [Supp. I] I-50-I-51.
"Gallium Tris(Salicylaldimine) Complexes Derived From Functionalized Tripodal Triamines", The Journal of Nuclear Medicine, vol. 32, 1991, by M. A. Green, et al., p. 944.
Ca 100(22): 175464q Woehrle et al., "Polymeric Schiff's base chelates & their precursors . . . ", Polymer Bulletin, 1984, 11(2), 151-8.
Green, "Synthesis and Biodistribution of a Series of Lipophilic ha-67 Tris(Salicylaldimine) Complexes," Journal of Labelled Compounds & Radiopharmaceuticals, vol. XXIII, Nos 10-12, pp. 1227-1229.

Primary Examiner—Robert L. Stoll
Assistant Examiner—John M. Covert
Attorney, Agent, or Firm—Barnes & Thornburg

[57] ABSTRACT

Radiopharmaceuticals for imaging myocardial tissues are prepared by forming lipophilic, cationic complexes of radioactive metal ions with metal chelating ligands comprising the Schiff base adducts of triamines and tetraamines with optionally substituted salicylaldehydes. The lipophilic, cationic, radioactive complexes of the invention exhibit high uptake and retention in myocardial tissues. Preferred gallium-68(III) complexes in accordance with this invention can be used to image the heart using positron emission tomography.

6 Claims, 3 Drawing Sheets n = 0, Ligand I
n = 1, Ligand II

FIG. 1 n = 0, Ligand I
n = 1, Ligand II

FIG. 2

$R_2, R_4 =$ H; $R_3 =$ OCH$_3$    Ligand III $R_2, R_4 =$ OCH$_3$; $R_3 =$ H    Ligand IV

FIG. 3

$R_2, R_4 =$ OCH$_3$    Ligand V

$R_2, R_4 =$ H    Ligand VI

FIG. 4

Ligand VIII

*FIG. 5*

R₂=R₄= H     Ligand VIII
R₂=R₄= OCH₃  Ligand IX

*FIG. 6*

RADIOPHARMACEUTICALS FOR IMAGING THE HEART

GOVERNMENT RIGHTS IN THE INVENTION

This invention was made with Government support under Grant DE-FG02-89ER60868 awarded by the Department of Energy and also under Grant R01-CA46909 awarded by the National Institute of Health. The Government has certain rights in this invention.

FIELD OF THE INVENTION

This invention relates to novel radiopharmaceuticals and their use for tissue imaging. More particularly this invention is directed to novel metal ion chelating ligands, their cationic lipophilic complexes with radioactive metal ions and the use of such complexes for imaging the heart.

BACKGROUND AND SUMMARY OF THE INVENTION

The use of radiopharmaceuticals for diagnostic imaging has evolved significantly over the last decade. There has been a substantial research and development effort directed not only to identification and development of radiopharmaceutical agents themselves, but as well to the development of the electronics hardware used for detecting and displaying radiotracer images of targeted organs/tissue. While tissue imaging techniques have been developed utilizing a wide variety of radioactive elements, those that have received most attention are radiopharmaceuticals formed with gamma or positron emitting radionuclides. The use of positron emitting radiopharmaceuticals has been of particular research interest. Indeed, positron emission tomography ("PET") has been shown to be a most powerful medical imaging technique that can quantitatively map the spatial distribution of positron-emitting nuclides inside the living body. Currently, PET imaging studies of regional perfusion in the brain and heart have found applications both in biomedical research and in clinical practice. In studies of the heart with PET, assessment of myocardial perfusion and perfusion reserve after exercise or pharmacologic coronary vasodilation has been useful both diagnostically and for research evaluation of patients with coronary artery disease.

The clinical applications of PET and other radiotracer imaging techniques have been limited both by the availability of the required radionuclides and by the inherent biodistribution properties of radiopharmaceutical agents. Thus, for example, high definition imaging of heart tissue requires not only efficient myocardial uptake of the radiopharmaceutical agent but, as well, retention of the radioactivity in the targeted issue. The ideal radiopharmaceutical agent exhibits a biodistribution pattern which will provide higher concentrations of the radiopharmaceutical in the targeted tissue relative to the blood levels and relative to radiopharmaceutical concentration in adjacent non-targeted tissues. Thus, the significant properties of radiopharmaceuticals designed for imaging the heart are high myocardial tissue uptake, good heart/blood ratios, and prolonged retention of the radiopharmaceutical concentrations in the myocardial tissues relative to that in the blood and of other tissues/organs in the thoracic cavity.

It is one object of this invention to provide metal chelating ligand intermediates for the production of radiopharmaceuticals uniquely adapted for myocardial imaging.

It is another object of this invention to provide lipophilic, cationic, radioactive metal complexes for radiotracer imaging of the heart.

Still another, more specific embodiment of this invention is the preparation and use of positron emitting, lipophilic, cationic complexes for myocardial imaging.

Those and other embodiments of this invention are achieved by use of bis(salicylaldimine) type ligands derived from linear triamines or tetraamines. The novel ligands are used to prepare physiologically stable, lipophilic, cationic complexes with radioactive metal ions ($M^{+i}$, $i \geq 3$) which complexes exhibits biodistribution characteristics favorable for myocardial tissue imaging. The ligand complexing radioactive metal ions can be gamma emitters or more preferably, positron emitters, including most preferably gallium or indium positron-emitting radionuclides. The cationic complexes in accordance with this invention exhibit kinetic inertness toward exchange with the plasma protein transferrin and are stable in aqueous solutions at physcological pH.

Following intravenous injection the radioactive cationic complexes in accordance with this invention exhibit significant uptake into myocardial tissues. The rapid myocardial uptake is followed by prolonged mycocardial retention relative to blood and other proximal tissues, allowing delayed imaging as well as prolonged image acquisition. Preferred radiopharmaceuticals in accordance with this invention are positron emitting gallium-68 cationic complexes which, when used in conjunction with a $^{68}Ge/^{68}Ga$ parent/daughter radionuclide generator system, will allow PET imaging studies of the heart, avoiding the expense associated with operation of an in-house cyclotron for radionuclide production.

DETAILED DESCRIPTION OF THE INVENTION

In accordance with this invention radiopharmaceuticals suitable for imaging myocardial tissue are prepared by reacting and complexing radionuclide metal ions of the formula $M^{+i}$ wherein i is an integer $\geq 3$ with a metal chelating ligand $L^{-l}$ wherein l is the effective anionic valence for L (typically 2 for the bis(salicylaldimine) ligands under the herein described reaction conditions for complex formation) to form a lipophilic, cationic, radioactive complex represented by the general formula $M(L)^{+(i-l)}$ which can be isolated as its salt with a physiologically acceptable counter ion.

The metal chelating ligand (L) used to prepare the radioactive cationic complexes of this invention are multidentate ligands of the formula wherein
n and n' are independently 0, 1 or 2;

$R_1$ and $R'_1$ are independently hydrogen or $C_1$-$C_4$ alkyl;

$R_7$ and $R_8$ are independently hydrogen or $C_1$-$C_4$ alkyl, or $R_7$ and $R_8$ taken together with the N and C atoms to which they are bonded form the group —N=CH—;

W is selected from the group consisting of wherein $R_5$ and $R'_5$ are independently hydrogen or $C_1$-$C_4$ alkyl, or $R_5$ and $R'_5$ taken together form a divalent group of the formula QCH<, and q is 0, 2 or 3; and Q is a group of the formula wherein $R_2$, $R_3$ and $R_4$ are independently hydrogen, halo, $C_1$-$C_4$ alkyl, $C_2$-$C_4$ alkenyl, $C_1$-$C_4$ alkoxy, or the group —$NR_9R'_9$ wherein $R_9$ and $R'_9$ are independently hydrogen, $C_1$-$C_4$ alkyl or phenyl;

and the corresponding phenolate anions formed by deprotonation of said ligands;

provided that when W is —$NR_5(CH_2)_{2\,4\,2}NR_5$—, and n and n' are 0, at least one of $R_2$, $R_3$ and $R_4$ is other than hydrogen.

Generally those compounds are salicylaldimine ligands derived by the condensation of salicylaldehyde or substituted salicylaldehydes with art-recognized linear triamines or tetraamines of the formula wherein $R_1$, $R'_1$, n, n' and W are as defined above. The Schiff base type metal chelating ligands of this invention (those ligands wherein $R_7$ and $R_8$ taken together with the N and C atoms to which they are bonded form the group —N=CH=) are prepared by condensation of the triamine or tetraamine intermediates with the required equivalents of a salicylaldehyde of the formula Q—CHO wherein Q is as defined above.

The linear tetraamine intermediates of the formula wherein W is the group $NH(CH_2)_qNH$— react with three equivalents of salicylaldehyde or a substituted salicylaldehyde to form tris(salicylaldimine) derivatives wherein $R_5$ and $R'_5$ are taken together to form a divalent group of the formula QCH<.

Examples of preferred linear tetraamines for use in preparing the present ligands include N,N'-bis(aminopropyl)ethylenediamine and N,N'-bis(3-amino-2,2-dimethylpropyl)ethylenediamine. Examples of preferred salicylaldehydes include salicylaldehyde; 4,6-dimethoxy salicylaldehyde; 4-methoxy salicylaldehyde, 5-methoxy salicylaldehyde and 4-diethylamino salicylaldehyde.

The Schiff base tris(salicylaldimine) or bis(salicylaldimines) ligands are themselves a preferred group of metal chelating ligands for preparation of the radiotracer complexes in accordance with the present invention. Those Schiff base ligands can, however, be reduced using, for example, an excess of sodium borohydride to provide the corresponding amines represented by the above formula wherein $R_7$ and $R_8$ are each hydrogen. The reduced compounds are likewise used to form radioactive complexes in accordance with this invention exhibiting good myocardial tissue uptake and retention.

In defining the metal chelating ligands in accordance with this invention, the term "halo" is intended to include fluoro, chloro, bromo, and iodo. "$C_1$-$C_4$ alkyl" includes methyl, ethyl, n-propyl, isopropyl, and butyl. "$C_2$-$C_4$ alkenyl" includes vinyl, propenyl, and butenyl. The term "$C_1$-$C_4$ alkoxy" includes methoxy, ethoxy, propoxy, sec-butoxy and the like.

The radioactive cationic ligand complexes of the general formula $M(L)^{+i-l}$ are prepared by reacting a metal chelating ligand as described above with a source of the radioactive metal ion $M^{+i}$ in ethanol or aqueous solution typically in the presence of an acetate buffer. The source of the radioactive metal ion can be any soluble salt or a weak or moderately stable, but kinetically labile, complex (for example, an acetylacetonato metal ion complex) which serves as the source of the metal ion for exchange with the metal ion chelating ligand in accordance with this invention. To facilitate purification of the radioactive ligand complex, or more specifically a salt of the cationic complex, a salt source of a physiologically acceptable counter ion, for example, chloride or iodide, is typically added to the complex-forming reaction mixture so that the purified complex has the general formula $M(L)^{+i-l}X_n^{-x}$ wherein $X_n^{-x}$ is the counter ion and $|(n)(-x)| = |i-1|$.

Any of a wide variety of radioactive metal ions can be used to form the cationic, lipophilic complexes of the present invention. Preferably the radioactive metal ion is a positron emitter having a charge of +3 or greater. Preferred are the positron emitting isotopes of gallium and indium. Gallium-68(III) is a most preferred positron emitting metal ion for forming the cationic complexes in accordance with the invention.

The radionuclide complexes of this invention are cationic and at the same time, lipophilic—having an actanol/water partition coefficient (P) exceeding 1 (log P>0). Generally it has been found that when the metal chelating ligand is derived from a linear tetraamine, sufficient lipophilic character is exhibited by the radionuclide ligand complex where there is a total of at least 7 carbons in the nitrogen-linking alkyl chains of the linear tetraamine. Where there are only 6 carbon atoms in the nitrogen-linking alkyl chains, the Schiff-base forming salicylaldehyde must be selected so that at least one of the substituents $R_2$, $R_3$, or $R_4$ is other than hydrogen to achieve the requisite degree of lipophilicity (log P>0) in the end product metal complex.

Gallium-67 has been substituted for gallium-68 (or other positron-emitting gallium or indium radionuclides) for animal studies to demonstrate the biodistribution properties of these radiopharmaceuticals. The gallium-67 complexes are prepared by ligand exchange from gallium-67 chloride, employing the tris-(acetylacetonato)gallium(III) complex as an intermediate. The Ga-67 acetylacetonate in ethanol is reacted with the chelating ligand or ligand precursor at elevated temperature to form rapidly the desired gallium radiopharmaceutical. The resulting complexes are lipophilic (log P>0 where P is the ocatanol/water partition coefficient) and migrate as single radioactive peak in thin layer chromatography studies—documenting their radiochemical purity. The biodistribution of several radiopharmaceuticals was determined in rats following intravenous injection using techniques previously described (M. A. Green, *Nuclear Medicine and Biology* 14:59-61, 1987; E. John and M. A. Green, *J. Medicinal Chemistry*, 33:1764-1770, 1990). The results of these rat biodistribution studies demonstrate that the present radiopharmaceuticals provide significant myocardial uptake of the gallium radiotracer; excellent heart/blood and heart/lung ratios; satisfactory heart/liver ratios; and prolonged myocardial retention of the gallium radioactivity.

The radiopharmaceutical complexes are used in accordance with the present method for imaging myocardial tissue. The complexes can be purified, for example, by chromatographic techniques. They are formulated into aqueous solutions suitable for intravenous administration using standard techniques for preparation of parenteral diagnostics. An aqueous solution of the present complexes can be sterilized, for example, by passage through a commercially available 0.2 micron filter. The complexes are typically administered intravenously in an amount effective to provide mycocaridal tissue concentrations of the radionuclide complex sufficient to provide the requisite photon (gamma/positron) flux for imaging the tissue. The dosage level for any given complex of this invention to achieve acceptable tissue imaging depends on its particular biodistribution and the sensitivity of the tissue imaging equipment. Effective dosage levels can be ascertained by routine experimentation. They typically range from about 1 to about 50 millicuries. Where the complexes are gallium-68 complexes for PET imaging of myocardial tissue, adequate photon fluxes can be obtained by intravenous administration of from about 1 to about 30 millicuries of the complex. Myocardial tissue is readily imaged using standard PET imaging equipment.

EXAMPLES

Figure 1:
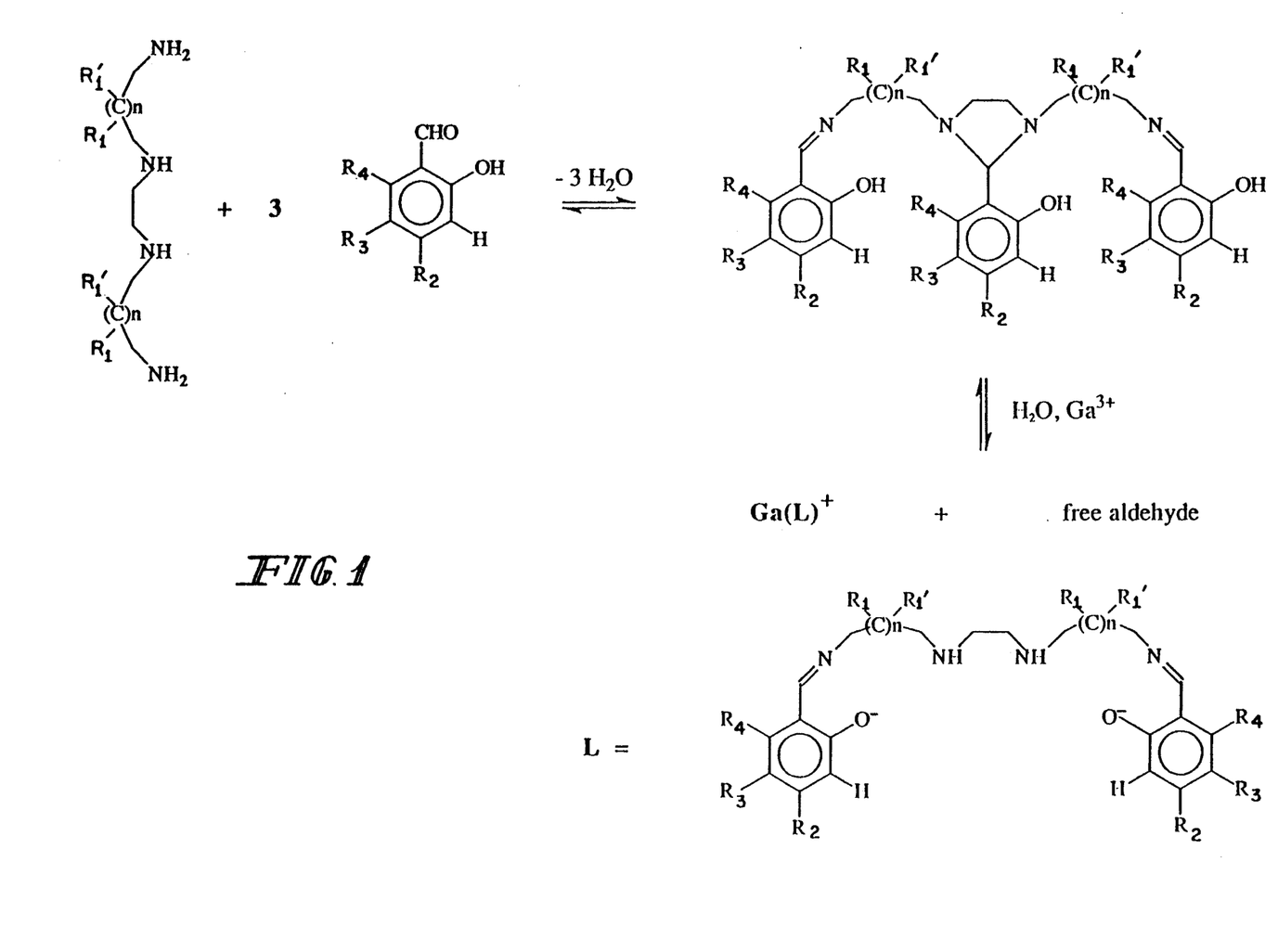
FIG. 1 illustrates the preparation of the tris(salicylaldimine) ligands of this invention and the formation of their gallium (III) complexes.
Figure 2:
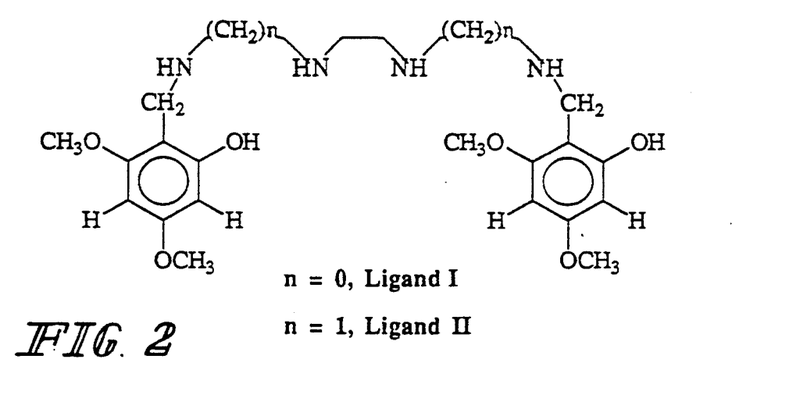
FIGS. 2–6 illustrate their five-coordinate and six-coordinate ligands for preparing the present radiotracer complexes.
Figure 3:
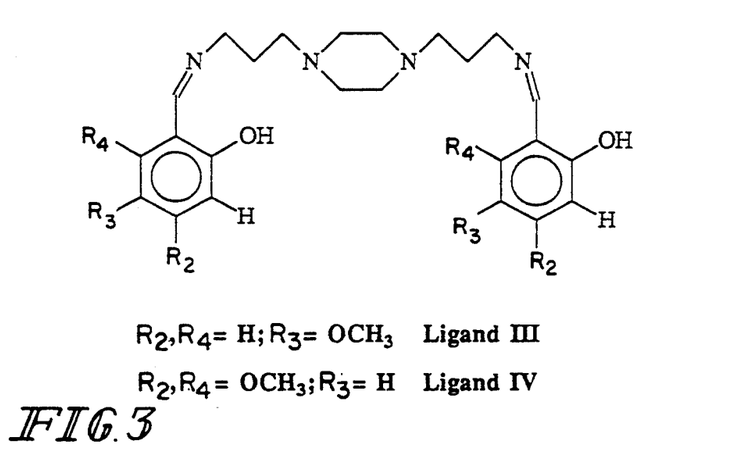
Figure 4:
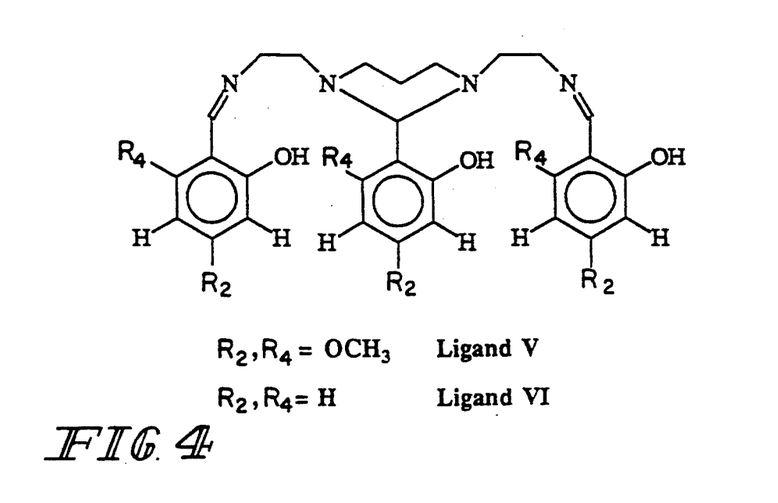
Figure 5:
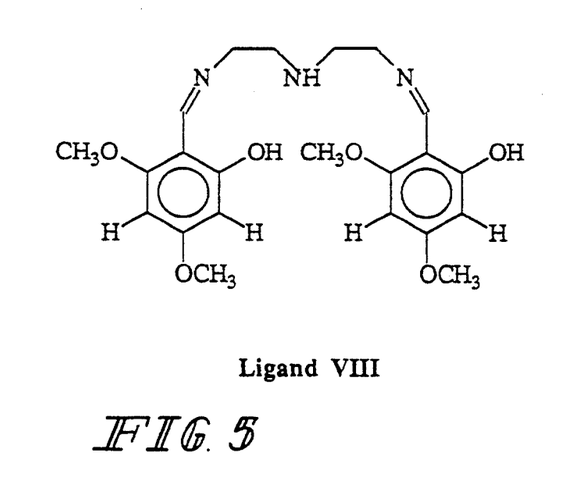
Figure 6:
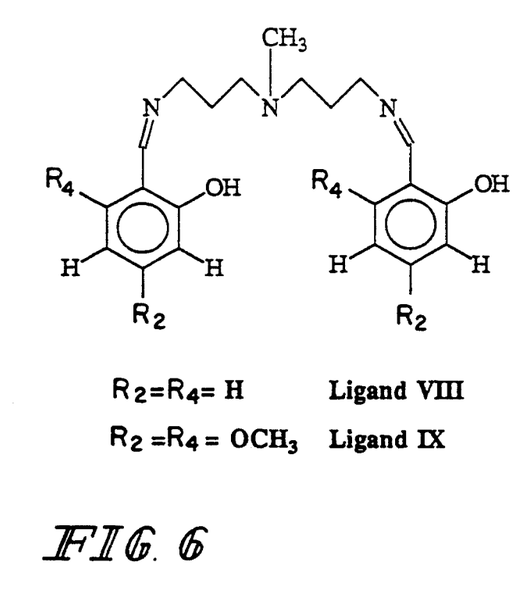

Salicylaldehydes, triethylenetriaamine, and N,N'-bis(3-aminopropyl)-ethylene-diamine were purchased from Aldrich Chemical Co. Ga(acac)$_3$ was purchased from Strem Chemical Co. A literature method for the synthesis of tetraamines was used for the synthesis of N,N'-bis(3-amino-2,2-dimethylpropyl)-ethylenediamine (DM-BAPEN) (Murmann, K. *Inorganic Syntheses* 1966, 8, 173). The tris(salicylaldimines) were synthesized by the general condensation reaction of three mole equivalents of aldehyde with the tetraamine (DasSarma B., Bailar, J. C. *J. Am. Chem. Soc.* 1955, 77, 5476.). Ga(acac)$_3$ reacts with the tris(salicylaldimine) in wet ethanol to give the corresponding Ga-bis(salicylaldimino)complex as shown in FIG. 1. The values for n and R substituents and ligand abbreviations corresponding to FIG. 1 are given in Table 1.

TABLE 1

Tris(salicylaldimine) ligands synthesized. Values for n and R$_n$ refer to the labels given in FIG. 1.

| Ligand Abbreviations | n/n' | R$_1$/R'$_1$ | R$_2$ | R$_3$ | R$_4$ |
|---|---|---|---|---|---|
| (4,6-MeO$_2$sal)$_3$-TETA | 0 | — | OMe | H | OMe |
| (sal)$_3$-BAPEN | 1 | H | H | H | H |
| (5-MeOsal)$_3$-BAPEN | 1 | H | H | OMe | H |
| (4-MeOsal)$_3$-BAPEN | 1 | H | OMe | H | H |
| (4,6-MeO$_2$sal)$_3$-BAPEN | 1 | H | OMe | H | OMe |
| (4-deasal)$_3$-BAPEN | 1 | H | NEt$_2$ | H | H |
| (4,6-MeO$_2$sal)$_3$-DM-BAPEN | 1 | Me | OMe | H | OMe |
| (4-deasal)$_3$-DM-BAPEN | 1 | Me | NEt$_2$ | H | H |

Tris(salicylaldimine) Synthesis:
H$_3$[(4,6-MeO$_2$-sal)$_3$BAPEN]

To a solution of 1.00 g of 4,6-dimethoxybenzaldehyde (5.49 mmol) in 15 mL of dry methanol was added 0.32 g of N,N'-bis(3-aminopropyl)ethylenediamine (1.84 mmol) in 15 mL of dry methanol. The mixture was refluxed for 20 minutes, then allowed to stir until cooled to 25° C. The solvent was removed by rotoevaporation. The resulting yellow oil was triturated with diethyl ether. Unreacted aldehyde immediately precipitated out and was filtered off. The filtrate was cooled to 0° C. for approximately 24 hours. The bright yellow product that had precipitated was filtered and washed with cold diethyl ether. 40% yield, melting point 70°-71° C.

$^1$H-NMR at 500 MHz in deuterated chloroform with TMS as reference: δ(ppm) 1.81 (m,8H) —CH$_2$—N—CH$_2$—; 2.53 (m, 4H) —C—CH$_2$—C—; 3.43 (m, 4H) =N—CH$_2$—; 3.70, 3.72, 3.76 3.78 (s, 18H) —OCH$_3$; 4.32 (s, 1H) —N—CH—N—; 5.73 (m, 4H) C$_6$H$_2$; 5.97 (m, 2H) C$_6$H$_2$; 8.28 (m, 2H); CH=N—. IR (KBr disk) v(C=N) 1625 cm$^{-1}$. The fast-atom bombardment mass spectrum in positive-ion mode (DTT/DTE matrix) showed [M+H]$^+$ at m/z=667 for M=C$_{35}$H$_{46}$N$_4$O$_9$.

All other ligands were synthesized using the same procedure described above. Work-up of the product, however, did vary. Instead of precipitation of solids from diethyl ether, (sal)$_3$-BAPEN, (4-MeOsal)$_3$-BAPEN, and (4-deasal)$_3$-DM-BAPEN were isolated as oils containing small amounts of unreacted aldehyde. The free aldehyde was observed in the $^1$H-NMR spectra as the only impurity. Analytical data obtained on the compounds are listed in Table 2.

TABLE 2

Tris(salicylaldimine) Ligands and Their Characterization Data.

| Ligand | [M + H]$^+$ FAB-MS | IR v(C=N) | $^1$H-NMR 500 MHz (CDCl$_3$,tms), δ(ppm) |
|---|---|---|---|
| (4,6-MeO$_2$sal)$_3$-TETA | 639 m/z | 1629 cm$^{-1}$ | 2.62(m, 4H), 2.93(m, 2H), 3.37(m,2H), 3.49 (m,4H) —CH$_2$—; 3.73 (m,6H), 3.77 (m,12H)—OCH$_3$; 4.49 (s,1H) —N—CH—N—; 5.63–6.04 (m, 6H) C$_6$H$_2$; 8.30 (m, 2H) —CH=N— |
| (sal)$_3$-BAPEN | | | 1.84 (m, 4H), 2.33 (m, 2H), 2.60 (m, 4H), 3.46 (m, 4H), 3.67 (m, 2H) —CH$_2$—; 3.63 (s, 1H) —N—CH—N—; 7.00 (m, 12H) C$_6$H$_4$; 8.13 (s, 2H) —CH=N— |
| (5-MeOsal)$_3$-BAPEN | 577 m/z | 1635 cm$^{-1}$ | 1.86 (m, 4H), 2.71 (m, 8H), 3.70 (m, 4H) —CH$_2$—; 3.77 (m, 9H) —OCH$_3$; 3.79 (s, 1H) —N—CH—N—; |

TABLE 2-continued

Tris(salicylaldimine) Ligands and Their Characterization Data.

| Ligand | [M + H]+ FAB-MS | IR ν(C=N) | $^1$H-NMR 500 MHz (CDCl$_3$,tms), δ(ppm) |
|---|---|---|---|
| (4-MeOsal)$_3$-BAPEN | | | 6.70–6.94 (m, 9H) C$_6$H$_3$; 8.30 (s, 2H) —CH=N— 1.81 (m, 4H), 2.28 (m, 2H), 2.50 (m, 2H), 2.67 (m, 4H), 3.58 (m, 2H), 3.41 (m, 2H) —CH$_2$—; 3.70 (s, 3H), 3.80 (s,6H) —OCH$_3$; 3.81 (s, 1H) —N—CH—N—; 6.21–6.42 (m, 6H), 6.77–7.10 (m, 3H) C$_6$H$_3$; 8.14 (m, 2H) —CH=N— |
| (4,6-MeO$_2$sal)$_3$-BAPEN | 667 m/z | 1625 cm$^{-1}$ | 1.81 (m, 8H) —CH$_2$—N—; 2.53 (m, 4H) —C—CH$_2$—; 3.43 (m, 4H) =N—CH$_2$—; 3.70–3.78 (m, 18H) —OCH$_3$; 4.32 (s,1H) —N—CH—N—; 5.73 (m, 4H), 5.97 (m,2H) C$_6$H$_2$; 8.28 (m, 2H) CH=N |
| (4-deasal)$_3$-BAPEN | 700 m/z | 1621 cm$^{-1}$ | 1.15 (m, 18H) —CH$_3$; 1.75(m,4H), 2.24(m,2H), 2.45(m,2H), 2.68 (m,2H) 3.52(m,6H) —CH$_2$—; 3.40 (m, 12H) φ-N—CH$_2$—; 3.49(s,1H) —N—CH—N—; 6.00–6.19 (m,6H), 6.70–6.90 (m, 3H) C$_6$H$_3$; 7.67 (m, 2H) —CH=N— |
| (4,6-MeO$_2$sal)$_3$-DM-BAPEN | | 1624 cm$^{-1}$ | 0.82 (s,6H), 0.85 (s, 6H) —CH$_3$; 2.25(m,2H), 2.52(m,6H), 2.65(m,2H), 2.92(m,2H), 3.30 (m,6H) —CH$_2$—; 3.72 (m, 6H), 3.76 (s, 12H) —OCH$_3$; 4.43 (s, 1H) —N—CH—N—; 5.55–6.00 (m, 6H) C$_6$H$_2$; 8.14 (m, 2H) —CH=N— |
| (4-deasal)$_3$-DM-BAPEN | | | 0.93 (s, 12H) —CH$_3$; 1.16 (m, 18H) —CH$_3$; 2.18–2.93 (m, 8H) —CH$_2$—; 3.26–3.43 (m, 17H) —CH$_2$—, —N—CH—N—; 5.99–6.96 (m, 9H) C$_6$H$_3$; 7.80 (m, 2H) —CH=N— |

Nine other six-coordinate and five-coordinate ligands (See FIGS. 2-6, Ligands I–IX) have been synthesized and characterized by $^1$H-NMR. Tables 3 and 4 give the NMR data obtained Ligands I and II were synthesized by borohydride reduction of (4,6-MeO$_2$sal)$_3$-TETA and (4,6-MeO$_2$sal)$_3$-BAPEN resulting in reduction of the two imine bonds to amine bonds (—CH=N—→—CH$_2$—NH—) and hydrolysis of the bridging imino groups. A 10-fold excess of NaBH$_4$ is added to an ethanol solution containing the tris-salicyladimine. The mixture is stirred at room temperature for 12 hours. The ethanol is removed and the white residue is washed with H$_2$O and diethyl ether. Disappearance of the ν(C=N) stretch in the FTIR spectrum was also used as evidence of the reduction of the imine bonds.

Ligands III–IX were synthesized as described previously for the tris(salicylaldimines).

TABLE 3

Additional 6-Coordinate Ligands and Characterization Data

| LIGAND | $^1$H-NMR 500 MHz (CDCl$_3$, tms), δ(ppm) |
|---|---|
| I | 2.47–2.63 (m, 8H) —CH$_2$—; |
| N,N'-bis(4,6-dimethoxy-2-hydroxybenzaldehyde)-triethylenetetraamine | 3.60–4.02 (m, 20H) —OCH$_3$, —CH$_2$—; 5.90–6.08 (m, 4H) C$_6$H$_2$; |
| II bis(4,6-dimethoxy-2-hydroxy-benzaldehyde)-N,N'-bis(3-aminopropyl)ethylenediamine | 1.08 (m, 2H), 1.69 (m, 2H), 2.65 (m, 8H) —CH$_2$—; 3.59–3.96 (m, 20H) —OCH$_3$, —CH$_2$—; 5.88–6.15 (m, 4H) C$_6$H$_2$ |
| III 1,4-bis(3-(5-methoxysalicylaldimino)propyl) piperazine | 1.86 (m, 4H), —C—CH$_2$—C—; 2.39–2.50 (m, 12H) —CH$_2$—N—; 3.61 (m, 4H) =N—CH$_2$—; 3.75 (s, 6H) —OCH$_3$; 6.74 (m, 2H), 6.88 (m, 4H) C$_6$H$_3$; 8.28 (s, 2H) —CH=N—; 12.97 (br, 2H) OH—N. |
| IV 1,4-bis(3-(4,6-dimethoxysalicylaldimino) propyl)piperazine | 1.81–242 (m, 16H), —CH$_2$—; 3.53 (m, 4H) —CH$_2$=N; 3.76 (m, 12H) —OCH$_3$; 5.55 (m, 2H), 5.85 (m, 2H) C$_6$H$_2$; 8.31 (m, 2H) —CH=N—; 14.10 (br, 2H) OH—N. |
| V tris(4,6-dimethoxysalicylaldimino)-2, 3, 2-tet [2, 3,-2-tet = N,N'-bis(2-aminoethyl)-1,3-propanediamine] | 1.75 (m, 4H), 2.35 (m, 2H), 2.77 (m, 2H), 3.04 (m, 2H) —CH2—; 3.70 (m, 18H) —OCH$_3$; 4.35 (m, 4H) —N—CH—N—; 5.04–6.05 (m, 6H) C6H2; 8.30 (m, 2H) —CH=N—. |
| VI tris(salicylaldimino)-2, 3, 2-tet [2,3,-2-tet = N,N'-bis(2-aminoethyl)-1,3-propanediamine] | 1.72 (m, 2H), 2.40 (m,2H), 2.57(m, 2H), 2.85 (m, 2H) 3.18 (m, 2H), 3.41 (m, 4H) —CH$_2$—; 3.91 (s,1H) —N—CH—N—; 7.29–7.75 (m, 12H) C$_6$H$_4$; 8.21 (m, 2H) —CH=N—. |

TABLE 4

5-Coordinate Ligands and Characterization Data.

| LIGAND | $^1$H-NMR 500 MHz (CDC13, TMS), δ(ppm) |
|---|---|
| VII N,N-bis[2-(4,6-dimethoxysalicylaldimino)ethylene]amine | 2.93 (t, 4H) —NCH2; 3.58 (t, 4H) —CH2—N=; 3.77, 3.78 (s, 12H) —OCH$_3$; 5.62 (m, 2H), 5.89 (m,2H) C$_6$H$_2$; 8.38 (m, 2H) —CH=N—. |
| VIII N-methyl-N, N-bis(3-salicylaldiminoproylene)amine | 1.86 (m, 4H) —C—CH2—C—; 2.23 (s, 3H) —N—CH$_3$; 2.43 (m, 4H) —CH$_2$, 3.63 (m, 4H) —CH$_2$—N=; 6.84–6.96 (m, 4H), 7.20—7.31 (m, 4H) C$_6$H$_3$; 8.34 (m, 2H) —CH=N—. |
| IX N-methyl-N, N-bis-[3-(4,6-dimethoxysalicylaldimino) proylene]amine | 1.83 (m, 4H) —C—CH2—C—; 2.20 (s, 3H) —N—CH$_3$; 2.44 (m, 4H) —CH2—N—; 3.53 (m, 4H) —CH2—N=; 3.74 (m, 12H) —OCH3; 5.55 (m,2H), 5.84 (m, 2H) C6H2; 8.29 (s, 2H) —CH=N—. |

Synthesis of Cold Gallium Complexes:
GaI[4,6-MeO$_2$-sal)$_2$BAPEN]+I−

A solution of 110 mg of Ga(acac)$_3$(0.3 mmol) in 10 mL of warm ethanol was added to 200 mg of (4,6-MeO$_2$sal)$_3$BAPEN (0.3 mmol) in 10 mL of warm ethanol. The mixture was heated to reflux for 30 minutes. 50 mg of KI in 1 mL of water was then added to the hot ethanol solution. The solution was slowly cooled to room temperature. The product precipitated out of solution as a white microcrystalline solid upon cooling. 86% yield, decomposes 298° C.

1H-NMR at 500 MHz in dimethylsulfoxide-d6 with TMS as reference: δ(ppm) 1.90 (m,2H), 2.55 (m, 2H) 2.62 (m, 2H), 2.95 (m, 4H), 3.32 (m, 4H), 3.63 (m, 2H) —CH2—; 3.74, 3.77 (s, 12H) —OCH3; 4.90 (br, 2H) —NH—; 5.85 (s, 2H), 5.93 (s, 2H) C6H2; 8.20 (s, 2H) —CH=N—. IR (KBr disk) ν(C=N) 1605 cm$^{-1}$. The fast-atom bombardment mass spectrum in positive-ion mode (DTT/DTE matrix) showed [M+H]+ at m/z=569 for [C26H26N4O6Ga]+.

Synthesis of Ga[(4-deasal)2BAPEN]+I−

The same procedure as above. 64% yield, decomposes at 285° C.

1H-NMR at 500 MHz in dimethylsulfoxide-d6 with TMS as reference: δ(ppm) 1.53 (m,2H), 1.92 (m, 2H) 2.63 (m, 2H), 2.92 (4H), 3.11 (m, 2H), 3.4 (m, 2H), 3.83 (m, 2H) —CH2—; 3.22 (m, 8H)-ϕ-N—CH2—; 4.86 (br, 2H) —NH—; 5.87 (m, 2H), 6.11 (m, 2H), 6.96 (m, 2H) C6H3; 7.89 (s, 2H) —CH=N—. IR (KBr disk) ν(C=N) 1596 cm$^{-1}$. The fast-atom bombardment mass spectrum in positive-ion mode (DTT/DTE matrix) showed [M+H]+ at m/z=579 for [C30H46N6O2Ga]+.

Synthesis of Radiolabeled Gallium Complexes

The gallium-67 labelled compounds were prepared by reaction of no-carrier-added [67Ga]-gallium(III)-tris-(acetylacetonate) with the appropriate tris(salicylaldimine) ligand (5 mg/ml in EtOH) in hot ethanol. This solution was diluted to a 5% ethanol concentration with saline and filtered through a 0.2 μm sterile polytetrafluoroethylene filter to deliver a product suitable for intravenous injection.

The radiochemical purity (>99%) was determined by thin layer chromatography on C18 silica gel plates eluted with methanol (R$_f$=0.1–0.2) and by paper chromatography on Whatman chromatography paper eluted with ethanol (R$_f$=0.8–1.0). The R$_f$ values were determined by analysis of the radiochromatograms with a Berthold Tracemaster 20 Automatic TLC Linear-Analyzer. Under these conditions, uncomplexed Ga$^{3+}$ and Ga(acac)3 remain at the origin. The cationic nature of the complexes was demonstrated by cellulose acetate electrophoresis in phosphate buffer at physiological pH.

Octanol/water partition coefficients were measured by vortex mixing 1 mL of 1-octanol and 1 mL of isotonic Tris buffer (pH 7.0) with a 1–5 μL sample of the radiolabeled gallium complex. Following centrifugation at >1200 g for 5 minutes, the octanol and aqueous phases were sampled and counted in an automatic well counter. The log P values for the 67GAL+ complexed ranged from 0.24–2.84 (Table 5).

Rat Biodistribution Studies

Under ether anesthesia, 1 to 3 μCi (0.1–0.2 mL) of no-carrier-added Ga-67 compound was administered by bolus injection into the femoral vein of male Sprague-Dawley rats. The ether anesthetized rats were sacrificed by decapitation at given time intervals post-injection, organs of interest were removed, weighed, and the gallium-67 activity counted. The biodistribution was calculated as a percentage of the injected dose per gram of tissue and percentage of injected dose per organ for each sample. The biodistribution data is summarized in Tables 6–13.

TABLE 5

Lipohilicity, and Myocardial Uptake of Gallium Tracers 67GaL+ Evaluated in Preliminary Studies

| Ligand | | | | | Ga-L$^{1+}$ | % injected dose in heart | | |
|---|---|---|---|---|---|---|---|---|
| n | R1 | R2 | R3 | R4 | log P | FW | 1 min | 2 h | Ligand Abbreviations |
| 0 | — | OCH3 | H | OCH3 | 0.24 | 542 | 0.55 ± 0.04 | 0.19 ± 0.03 | L = (4,6-MeO2Sal)2TETA |
| 1 | H | H | OCH3 | H | 0.53 | 510 | 0.34 ± 0.03 | 0.23 ± 0.03 | L = (5-MeOSal)2BAPEN |
| 1 | H | H | H | H | 0.56 | 450 | 0.45 ± 0.01 | 0.41 ± 0.03 | L = Sal2BAPEN |
| 1 | H | OCH3 | H | H | 0.80 | 510 | 0.67 ± 0.08 | 0.65 ± 0.05 | L = (4-MeOSal)2BAPEN |
| 1 | H | OCH3 | H | OCH3 | 1.68 | 570 | 1.04 ± 0.12 | 0.86 ± 0.11 | L = (4,6-MeO2Sal)2BAPEN |
| 1 | H | Et2N | H | H | 2.44 | 592 | 0.69 ± 0.05 | 0.65 ± 0.05 | L = (4-deaSal)2BAPEN |
| 1 | CH3 | OCH3 | H | OCH3 | 2.73 | 618 | 1.03 ± 0.17 | 1.01 ± 0.06 | L = (4,6-MeO2Sal)2DM-BAPEN |
| 1 | CH3 | Et2N | H | H | 2.84 | 639 | 0.66 ± 0.06 | 0.40 ± 0.04 | L = (4-deaSal)2DM-BAPEN |

TABLE 6

Rat Biodistribution Data for 67GaL+
L = [bis(4-methoxysalicylaldimino)-N,N'-bis(3-aminopropyl)-ethylenediamine]

| Organ | 1 min | 15 min | 120 min |
|---|---|---|---|
| | % Injected Dose per Organ | | |
| Blood | 4.44 ± 0.33 | 0.77 ± 0.06 | 0.42 ± 0.03 |
| Heart | 0.67 ± 0.08 | 0.73 ± 0.09 | 0.65 ± 0.05 |
| Lungs | 1.05 ± 0.13 | 0.45 ± 0.05 | 0.38 ± 0.03 |

TABLE 6-continued

Rat Biodistribution Data for $^{67}$GaL$^+$
L = [bis(4-methoxysalicylaldimino)-N,N'-bis(3-aminopropyl)-ethylenediamine]

| Organ | 1 min | 15 min | 120 min |
|---|---|---|---|
| Liver | 25.21 ± 1.25 | 14.65 ± 2.59 | 5.11 ± 1.35 |
| Spleen | 0.20 ± 0.03 | 0.12 ± 0.01 | 0.10 ± 0.02 |
| Kidney (one) | 8.42 ± 0.81 | 5.56 ± 0.72 | 1.69 ± 0.08 |
| Brain | 0.03 ± 0.01 | 0.01 ± 0.01 | 0.01 ± 0.001 |
| % Injected Dose per Gram Tissue | | | |
| Blood | 0.32 ± 0.02 | 0.06 ± 0.01 | 0.03 ± 0.01 |
| Heart | 0.96 ± 0.07 | 1.01 ± 0.08 | 0.92 ± 0.07 |
| Lungs | 0.91 ± 0.09 | 0.38 ± 0.05 | 0.32 ± 0.02 |
| Liver | 3.05 ± 0.27 | 1.71 ± 0.40 | 0.63 ± 0.20 |
| Spleen | 0.31 ± 0.05 | 0.22 ± 0.02 | 0.17 ± 0.03 |
| Kidney (one) | 11.08 ± 0.88 | 4.47 ± 0.62 | 2.19 ± 0.08 |
| Brain | 0.02 ± 0.01 | 0.01 ± 0.001 | 0.01 ± 0.003 |
| Heart/Blood | 2.99 ± 0.15 | 17.62 ± 0.31 | 30.58 ± 2.22 |
| Heart/Lungs | 1.06 ± 0.14 | 2.68 ± 0.14 | 2.93 ± 0.39 |
| Heart/Liver | 0.32 ± 0.05 | 0.62 ± 0.15 | 1.61 ± 0.66 |
| n = | 4 | 4 | 4 |

TABLE 8

Rat Biodistribution Data for $^{67}$GaL$^+$
L = [bis(salicylaldimino)-N,N'-bis(3-aminopropyl)-ethylenediamine]

| Organ | 1 min | 15 min | 120 min |
|---|---|---|---|
| % Injected Dose per Organ | | | |
| Blood | 4.21 ± 0.06 | 0.99 ± 0.06 | 0.64 ± 0.10 |
| Heart | 0.45 ± 0.01 | 0.44 ± 0.04 | 0.41 ± 0.03 |
| Lungs | 1.00 ± 0.09 | 0.30 ± 0.02 | 0.28 ± 0.04 |
| Liver | 26.71 ± 3.17 | 9.21 ± 1.28 | 5.30 ± 0.58 |
| Spleen | 0.16 ± 0.03 | 0.07 ± 0.01 | 0.06 ± 0.02 |
| Kidney (one) | 9.84 ± 0.65 | 3.56 ± 0.39 | 1.40 ± 0.25 |
| Brain | 0.03 ± 0.01 | 0.01 ± 0.001 | 0.01 ± 0.001 |
| % Injected Dose per Gram Tissue | | | |
| Blood | 0.30 ± 0.01 | 0.07 ± 0.01 | 0.05 ± 0.01 |
| Heart | 0.65 ± 0.02 | 0.60 ± 0.03 | 0.58 ± 0.05 |
| Lungs | 0.85 ± 0.09 | 0.29 ± 0.02 | 0.24 ± 0.03 |
| Liver | 3.27 ± 0.44 | 1.20 ± 0.16 | 0.64 ± 0.10 |
| Spleen | 0.27 ± 0.03 | 0.11 ± 0.01 | 0.11 ± 0.01 |
| Kidney (one) | 12.39 ± 0.55 | 4.47 ± 0.62 | 1.85 ± 0.30 |
| Brain | 0.02 ± 0.01 | 0.01 ± 0.001 | 0.01 ± 0.003 |
| Heart/Blood | 2.15 ± 0.05 | 8.34 ± 0.66 | 12.44 ± 0.42 |
| Heart/Lungs | 0.73 ± 0.10 | 2.08 ± 0.13 | 2.43 ± 0.18 |
| Heart/Liver | 0.20 ± 0.02 | 0.51 ± 0.06 | 0.93 ± 0.19 |
| n = | 4 | 4 | 4 |

TABLE 7

Rat Biodistribution Data for $^{67}$GaL$^+$
L = [bis(5-methoxysalicylaldimino)-N,N'-bis(3-aminopropyl)ethylenediamine]

| Organ | 1 min | 15 min | 120 min |
|---|---|---|---|
| % Injected Dose per Organ | | | |
| Blood | 7.55 ± 1.45 | 2.13 ± 0.54 | 1.11 ± 0.04 |
| Heart | 0.34 ± 0.03 | 0.26 ± 0.02 | 0.23 ± 0.03 |
| Lungs | 0.79 ± 0.16 | 0.24 ± 0.03 | 0.18 ± 0.01 |
| Liver | 26.46 ± 4.69 | 18.98 ± 6.48 | 6.79 ± 0.42 |
| Spleen | 0.15 ± 0.03 | 0.06 ± 0.01 | 0.04 ± 0.01 |
| Kidney (one) | 7.64 ± 0.16 | 3.61 ± 1.01 | 1.19 ± 0.05 |
| Brain | 0.04 ± 0.01 | 0.01 ± 0.001 | 0.01 ± 0.001 |
| % Injected Dose per Gram Tissue | | | |
| Blood | 0.52 ± 0.08 | 0.15 ± 0.04 | 0.08 ± 0.01 |
| Heart | 0.46 ± 0.03 | 0.36 ± 0.01 | 0.33 ± 0.03 |
| Lungs | 0.55 ± 0.14 | 0.22 ± 0.22 | 0.16 ± 0.02 |
| Liver | 3.01 ± 0.51 | 2.09 ± 0.78 | 0.78 ± 0.01 |
| Spleen | 0.25 ± 0.02 | 0.09 ± 0.01 | 0.07 ± 0.01 |
| Kidney (one) | 9.31 ± 0.32 | 4.65 ± 1.29 | 1.57 ± 0.13 |
| Brain | 0.02 ± 0.01 | 0.00 ± 0.00 | 0.00 ± 0.00 |
| Heart/Blood | 0.89 ± 0.12 | 2.61 ± 0.55 | 4.33 ± 0.28 |
| Heart/Lungs | 0.71 ± 0.11 | 1.71 ± 0.11 | 2.13 ± 0.13 |
| Heart/Liver | 0.15 ± 0.03 | 0.19 ± 0.05 | 0.42 ± 0.03 |
| n = | 4 | 4 | 4 |

TABLE 9

Rat Biodistribution Data for $^{67}$GaL$^+$
L = [bis(diethylaminosalicylaldimino)-N,N'-bis(2,2'-dimethyl-3-aminopropyl)ethylenediamine]

| Organ | 1 min | 15 min | 120 min |
|---|---|---|---|
| | % Injected Dose per Organ | | |
| Blood | 30.59 ± 3.45 | 5.08 ± 0.71 | 1.06 ± 0.20 |
| Heart | 0.66 ± 0.06 | 0.46 ± 0.04 | 0.40 ± 0.04 |
| Lungs | 5.30 ± 0.23 | 2.71 ± 0.22 | 1.31 ± 0.07 |
| Liver | 47.04 ± 6.53 | 50.24 ± 11.08 | 11.06 ± 2.46 |
| Spleen | 1.12 ± 0.34 | 2.29 ± 0.42 | 2.09 ± 0.18 |
| Kidney (one) | 4.25 ± 0.52 | 4.79 ± 0.38 | 5.17 ± 0.19 |
| Brain | 0.08 ± 0.02 | 0.00 ± 0.00 | 0.02 ± 0.01 |
| | % Injected Dose per Gram Tissue | | |
| Blood | 1.91 ± 0.22 | 0.30 ± 0.04 | 0.06 ± 0.01 |
| Heart | 0.85 ± 0.09 | 0.57 ± 0.05 | 0.47 ± 0.02 |
| Lungs | 4.23 ± 0.68 | 2.06 ± 0.21 | 1.02 ± 0.13 |
| Liver | 4.91 ± 0.36 | 4.78 ± 1.20 | 0.96 ± 0.14 |
| Spleen | 1.61 ± 0.44 | 3.15 ± 0.45 | 2.89 ± 0.21 |
| Kidney (one) | 4.85 ± 0.75 | 5.55 ± 0.50 | 5.28 ± 0.32 |
| Brain | 0.05 ± 0.01 | 0.02 ± 0.01 | 0.00 ± 0.00 |
| Heart/Blood | 0.45 ± 0.04 | 1.94 ± 0.33 | 8.06 ± 1.62 |
| Heart/Lungs | 0.20 ± 0.02 | 0.28 ± 0.04 | 0.46 ± 0.07 |
| Heart/Liver | 0.17 ± 0.03 | 0.13 ± 0.04 | 0.50 ± 0.07 |

TABLE 9-continued

Rat Biodistribution Data for $^{67}$GaL$^+$
L = [bis(diethylaminosalicylaldimino)-N,N'-bis(2,2'-dimethyl-3-aminopropyl)ethylenediamine]

| Organ | 1 min | 15 min | 120 min |
|---|---|---|---|
| n = | 4 | 4 | 4 |

TABLE 10

Rat Biodistribution Data for $^{67}$GaL$^+$
L = [bis(4,6-dimethoxysalicylaldimino)-N,N'-bis(2,2'-dimethyl-3-aminopropyl)-ethylenediamine]

| Organ | 1 min | 15 min | 120 min |
|---|---|---|---|
| | % Injected Dose per Organ | | |
| Blood | 18.76 ± 6.91 | 1.97 ± 0.15 | 0.45 ± 0.03 |
| Heart | 1.03 ± 0.17 | 0.93 ± 0.04 | 0.01 ± 0.06 |
| Lungs | 1.63 ± 0.47 | 0.75 ± 0.05 | 0.64 ± 0.06 |
| Liver | 50.62 ± 5.72 | 36.83 ± 2.91 | 3.91 ± 0.19 |
| Spleen | 1.07 ± 0.35 | 1.25 ± 0.20 | 0.97 ± 0.07 |
| Kidney (one) | 8.33 ± 0.80 | 8.77 ± 0.60 | 5.40 ± 0.24 |
| Brain | 0.10 ± 0.02 | 0.04 ± 0.01 | 0.04 ± 0.01 |
| | % Injected Dose per Gram Tissue | | |
| Blood | 1.30 ± 0.45 | 0.13 ± 0.01 | 0.03 ± 0.01 |
| Heart | 1.31 ± 0.17 | 1.23 ± 0.07 | 1.36 ± 0.09 |
| Lungs | 1.24 ± 0.20 | 0.63 ± 0.03 | 0.58 ± 0.06 |
| Liver | 5.82 ± 0.93 | 3.92 ± 0.20 | 0.42 ± 0.02 |
| Spleen | 1.59 ± 0.57 | 1.96 ± 0.32 | 1.59 ± 0.16 |
| Kidney (one) | 10.62 ± 0.94 | 10.49 ± 0.92 | 6.86 ± 0.54 |
| Brain | 0.06 ± 0.01 | 0.03 ± 0.01 | 0.02 ± 0.01 |
| Heart/Blood | 1.11 ± 0.40 | 9.65 ± 0.53 | 44.46 ± 1.63 |
| Heart/Lungs | 1.07 ± 0.12 | 1.96 ± 0.20 | 2.34 ± 0.14 |
| Heart/Liver | 0.23 ± 0.06 | 0.32 ± 0.02 | 3.24 ± 0.07 |
| n = | 4 | 4 | 4 |

TABLE 11

Rat Biodistribution Data for $^{67}$GaL$^+$
L = [bis(4,6-dimethoxysalicylaldimino)-N,N'-triethylene-tetraamine]

| Organ | 1 min | 15 min | 120 min |
|---|---|---|---|
| | % Injected Dose per Organ | | |
| Blood | 19.26 ± 2.97 | 9.32 ± 1.38 | 0.34 ± 0.02 |
| Heart | 0.55 ± 0.04 | 0.36 ± 0.03 | 0.19 ± 0.03 |
| Lungs | 1.17 ± 0.23 | 0.50 ± 0.05 | 0.10 ± 0.01 |
| Liver | 16.90 ± 1.70 | 20.33 ± 1.11 | 6.90 ± 1.07 |
| Spleen | 0.22 ± 0.01 | 0.11 ± 0.02 | 0.04 ± 0.01 |
| Kidney (one) | 3.83 ± 0.31 | 1.89 ± 0.40 | 0.42 ± 0.04 |
| Brain | 0.07 ± 0.01 | 0.04 ± 0.01 | 0.01 ± 0.01 |
| | % Injected Dose per Gram Tissue | | |
| Blood | 1.90 ± 0.56 | 0.71 ± 0.08 | 0.03 ± 0.01 |
| Heart | 0.76 ± 0.04 | 0.53 ± 0.06 | 0.28 ± 0.05 |
| Lungs | 0.97 ± 0.03 | 0.51 ± 0.05 | 0.08 ± 0.02 |
| Liver | 1.88 ± 0.15 | 2.42 ± 0.25 | 0.83 ± 0.15 |
| Spleen | 0.35 ± 0.02 | 0.18 ± 0.02 | 0.06 ± 0.01 |
| Kidney (one) | 4.36 ± 0.27 | 2.35 ± 0.41 | 0.51 ± 0.10 |
| Brain | 0.05 ± 0.01 | 0.03 ± 0.01 | 0.01 ± 0.01 |
| Heart/Blood | 0.53 ± 0.04 | 0.74 ± 0.03 | 10.29 ± 2.64 |
| Heart/Lungs | 0.79 ± 0.05 | 1.03 ± 0.20 | 3.49 ± 0.37 |
| Heart/Liver | 0.41 ± 0.04 | 0.22 ± 0.01 | 0.34 ± 0.05 |
| n = | 4 | 4 | 4 |

TABLE 12

Biodistribution of $^{67}$Ga[(4,6-MeO$_2$Sal)$_2$-3,2,3-tet]$^{1+}$ in Rats (178-217 g) Following Intravenous Injection {[(4,6-MeO)$_2$sal]$_2$-3,2,3-tet}$^{2-}$

| | % Injected Dose Per Gram of Tissue | | | |
|---|---|---|---|---|
| | 1 min | 5 min | 15 min | 120 min |
| Blood | 0.66 ± 0.14 | 0.11 ± 0.01 | 0.07 ± 0.01 | 0.03 ± 0.00 |
| Heart | 1.52 ± 0.24 | 1.45 ± 0.20 | 1.22 ± 0.12 | 1.37 ± 0.12 |
| Lungs | 0.81 ± 0.16 | 0.55 ± 0.05 | 0.42 ± 0.06 | 0.45 ± 0.11 |
| Liver | 4.72 ± 0.82 | 4.32 ± 0.53 | 2.19 ± 0.21 | 0.33 ± 0.01 |
| Spleen | 0.61 ± 0.09 | 0.52 ± 0.15 | 0.43 ± 0.06 | 0.37 ± 0.06 |
| Kidney (1) | 6.40 ± 0.92 | 6.10 ± 0.53 | 4.22 ± 0.30 | 2.77 ± 0.24 |
| Brain | 0.03 ± 0.01 | 0.01 ± 0.00 | 0.01 ± 0.00 | 0.01 ± 0.00 |
| Heart/Blood | 2.34 ± 0.36 | 13.28 ± 2.19 | 18.10 ± 0.91 | 45.58 ± 3.96 |
| Heart/Lung | 1.88 ± 0.18 | 2.64 ± 0.34 | 2.98 ± 0.53 | 3.27 ± 1.32 |
| Heart/Liver | 0.32 ± 0.03 | 0.34 ± 0.04 | 0.56 ± 0.10 | 4.12 ± 0.44 |
| | n = 7 | n = 7 | n = 4 | n = 4 |

TABLE 13

Biodistribution of $^{67}$Ga[4-deaSal)$_2$-3,2,3-tet]$^{1+}$ in Rats (175-212 g) Following Intravenous Injection {(4-deaSal)$_2$-3,2,3-tet}$^{2-}$

| | % Injected Dose Per Gram of Tissue | | | |
|---|---|---|---|---|
| | 1 min | 5 min | 15 min | 120 min |
| Blood | 0.80 ± 0.01 | 0.39 ± 0.05 | 0.20 ± 0.03 | 0.10 ± 0.01 |
| Heart | 0.98 ± 0.07 | 0.91 ± 0.06 | 0.90 ± 0.06 | 0.92 ± 0.10 |
| Lungs | 1.16 ± 0.06 | 0.89 ± 0.19 | 0.70 ± 0.07 | 0.53 ± 0.06 |
| Liver | 4.15 ± 0.25 | 3.96 ± 0.28 | 3.21 ± 0.25 | 1.07 ± 0.10 |
| Spleen | 1.22 ± 0.47 | 1.19 ± 0.17 | 1.27 ± 0.17 | 0.99 ± 0.18 |
| Kidney (1) | 7.22 ± 0.48 | 7.11 ± 0.89 | 6.82 ± 0.53 | 5.69 ± 0.75 |
| Brain | 0.04 ± 0.01 | 0.02 ± 0.01 | 0.02 ± 0.00 | 0.02 ± 0.01 |
| Heart/Blood | 1.22 ± 0.08 | 2.36 ± 0.25 | 4.54 ± 0.31 | 9.21 ± 1.12 |
| Heart/Lung | 0.85 ± 0.10 | 1.05 ± 0.19 | 1.29 ± 0.05 | 1.74 ± 0.35 |
| Heart/Liver | 0.24 ± 0.03 | 0.23 ± 0.02 | 0.28 ± 0.04 | 0.86 ± 0.18 |
| | n = 4 | n = 4 | n = 4 | n = 3 |

PET Imaging of the Heart with
$^{68}$Ga-bis(4,6-dimethoxysalicylaldimino)-N,N'-bis-(aminopropyl)ethylenediamine,
[$^{68}$Ga(4,6MeO$_2$sal)$_2$BAPEN]+

A PET imaging study with $^{68}$Ga-bis(4,6-dimethoxysalicylaldimino)-N,N'-bis(aminopropyl) ethylenediamine was conducted at Washington University School of Medicine, St. Louis, in collaboration with Professor Steven R. Bergmann, M.D., Ph.D. A normal mongrel dog anesthetized with thiopental and α-chloralose (i.v.) was intubated and ventilated with normal air. The dog was placed in a plexiglass holder and positioned within the PET VI camera, a positron emission tomograph that permits simultaneous acquisition of seven transverse tomographic slices with a slice-to-slice separation of 1.44 cm, a slice thickness of 1.39 cm, and a reconstructed resolution of 12.0 mm (full width at half maximum). A transmission scan, necessary for attenuation correction, was obtained using an external ring of $^{68}$Ge/$^{68}$Ga. A $^{15}$O-myocardial perfusion image was then obtained for reference employing $^{15}$O-water and $^{15}$O-carbon monoxide in a standard PET protocol. After decay of the $^{15}$O activity to background levels, the $^{68}$Ga-bis(4,6-dimethoxysalicylaldimino)-N,N'-bis-(aminopropyl) ethylene-diamine radiopharmaceutical (20 mCi) was administered to the dog as a bolus intravenous injection. Dynamic PET data was collected for ten 1 minute frames commencing at the time of $^{68}$Ga injection, followed by eight consecutive 10 minute static images. PET images of the chest were reconstructed from each of the ten one minute frames and each of the eight 10 minute frames. Beyond 20 minutes post-injection the heart was clearly delineated in the $^{68}$Ga-images with good heart-to-blood and heart-to-lung contrast. Regions-of-interest were defined in the $^{68}$Ga images allowing quantitative determination of regional myocardial tissue concentrations of tracer. No clearance of myocardial $^{68}$Ga radioactivity was observed over the 90 minute imaging period following injection of the $^{68}$Ga radiopharmaceutical, consistent with the myocardial retention of tracer previously observed in the rat.

We claim:

1. A cationic complex of the formula $M(L)^{+(i-2)}$ wherein M is a radioactive metal cation having a valence of +i wherein i is an integer $\geq 3$ and L is a metal chelating ligand of the formula wherein n and n' are independently 0, 1 or 2;

$R_1$ and $R'_1$ are independently hydrogen or $C_1$-$C_4$ alkyl;

$R_7$ and $R_8$ are independently hydrogen or $C_1$-$C_4$ alkyl, or $R_7$ and $R_8$ taken together with the N and C atoms to which they are bonded form the group —N=CH—;

W is selected from the group consisting of wherein $R_5$ and $R'_5$ are independently hydrogen or $C_1$-$C_4$ alkyl, or $R_5$ and $R'_5$ taken together form a divalent group of the formula QCH<, and q is 0, 2 or 3; and Q is a group of the formula wherein $R_2$, $R_3$ and $R_4$ are independently hydrogen, halo, $C_1$-$C_4$ alkyl, $C_2$-$C_4$ alkenyl, $C_1$-$C_4$ alkoxy, or the group —$NR_9R'_9$ wherein $R_9$ and $R'_9$ are independently hydrogen, $C_1$-$C_4$ alkyl or phenyl;

and the corresponding phenolate anions formed by deprotonation of said ligands;

provided that when W is —$NR_5(CH_2)_{\geq 2}NR_5$—, and n and n' are 0, at least one of $R_2$, $R_3$ and $R_4$ is other than hydrogen; and when W is —$NR_5$—, and n and n' are 1, at least one of $R_2$, $R_3$ and $R_4$ is other than hydrogen or halo.

2. The cationic complex of claim 1 wherein the radioactive metal cation is a positron emitter.

3. The cationic complex of claim 1 formed with a source of gallium-68(III).

4. A method for imaging the heart in a warm-blooded vertebrate comprising the steps of administering intravenously to said vertebrate a cationic complex of the formula $M(L)^{+(i-2)}$ wherein M is a radioactive metal cation having a valence of +i wherein i is an integer $\geq 3$ and L is a metal chelating ligand of the formula wherein n and n' are independently 0, 1 or 2;

$R_1$ and $R'_1$ are independently hydrogen or $C_1$-$C_4$ alkyl;

$R_7$ and $R_8$ are independently hydrogen or $C_1$-$C_4$ alkyl, or $R_7$ and $R_8$ taken together with the N and C atoms to which they are bonded form the group —N=CH—;

W is selected from the group consisting of wherein $R_5$ and $R'_5$ are independently hydrogen or $C_1$-$C_4$ alkyl, or $R_5$ and $R'_5$ taken together form a divalent group of the formula QCH<, and q is 0, 2 or 3; and Q is a group of the formula wherein $R_2$, $R_3$ and $R_4$ are independently hydrogen, halo, $C_1$-$C_4$ alkyl, $C_2$-$C_4$ alkenyl, $C_1$-$C_4$ alkoxy, or the group —$NR_9R'_9$ wherein $R_9$ and $R'_9$ are independently hydrogen, $C_1$-$C_4$ alkyl or phenyl;

and the corresponding phenolate anions formed by deprotonation of said ligands;

provided that when W is —$NR_5(CH_2)_{\geq 2}NR_5$—, and n and n' are 0, at least one of $R_2$, $R_3$ and $R_4$ is other than hydrogen said complex being administered in an amount effective to provide an imageable concentration of said complex in myocardial tissue of said vertebrate, and detecting the pattern of radioactivity of the cationic complex in said tissue.

5. The method of claim 4 wherein the cationic complex is formed with a positron emitting radioactive metal cation and the tissue is imaged with a camera for positron emission tomography.

6. The method of claim 4 wherein the positron emitting radioactive metal cation is gallium-68(III).